United States Patent [19]
Cooper

[11] Patent Number: 5,389,392
[45] Date of Patent: Feb. 14, 1995

[54] ESTERIFIED POLYETHER FAT MIMETICS CONTAINING RING-OPENED OXOLANE UNITS

[75] Inventor: Charles F. Cooper, Paoli, Pa.

[73] Assignee: Arco Chemical Technology, L.P., Del.

[21] Appl. No.: 179,847

[22] Filed: Jan. 11, 1994

Related U.S. Application Data

[63] Continuation of Ser. No. 886,583, May 20, 1992, abandoned, which is a continuation-in-part of Ser. No. 633,814, Dec. 27, 1990, abandoned.

[51] Int. Cl.$^6$ .................................................. A23L 1/00
[52] U.S. Cl. ...................................... 426/531; 426/601; 426/611; 554/161; 554/227
[58] Field of Search ............... 426/531, 601, 603, 606, 426/607, 611; 554/161, 162, 163, 164, 165, 168, 169, 172, 227, 228; 536/18.3

[56] References Cited

U.S. PATENT DOCUMENTS 5,308,634  5/1994  Cooper ................................. 426/531

Primary Examiner—Donald E. Czaja
Assistant Examiner—Leslie Wong
Attorney, Agent, or Firm—Stephen D. Harper

[57] ABSTRACT

Esterified polyethers containing ring-opened oxolane units are useful as reduced calorie fat substitutes in food compositions due to their resistance to enzymatic hydrolysis and absorption upon ingestion. The fat mimetics have improved thermal and oxidative stability as compared to known propylene oxide-based fat substitutes.

20 Claims, No Drawings

ESTERIFIED POLYETHER FAT MIMETICS CONTAINING RING-OPENED OXOLANE UNITS

This is a continuation of application Ser. No. 07/886,583, filed May 20, 1992, now abandoned, which is a continuation-in-part of application Ser. No. 07/633,814, filed Dec. 27, 1990, now abandoned.

FIELD OF THE INVENTION

This invention relates to esterified polyethers containing oxytetramethylene units (.e., ring-opened oxolane units) which are useful as fat mimetics in food compositions. The novel fat mimetics of the invention have good organoleptic characteristics and physical properties resembling those of naturally occurring edible oils and fats, but are substantially non-digestible and hence suitable for reducing the available caloric content of a food composition without altering the mouth feel and consistency of the composition. The esterified polyethers have the additional advantage of increased thermal and oxidative stability as compared to esterified propoxylated polyols not containing oxytetramethylene units.

BACKGROUND OF THE INVENTION

The accumulation of medical evidence in recent years regarding the adverse health implications of high fat diets, principally heart attacks, arteriosclerosis and obesity, has caused consumers to become extremely concerned about their diets. It is estimated that between 70–80% of U.S. adult females follow a weight reducing diet at least once a year. Men are also concerned about their weight and cholesterol levels.

Common obesity is currently one of the most prevalent metabolic problems in the general population. Fats and oils are necessary for balanced nutrition. However, the average consumer simply consumes more than is needed for proper nutrition. It is estimated that lipids constitute about 40% of the total calories in the typical Western diet. Fats are consumed directly in meats, spreads, salad oils, and in natural produce such as nuts and avocados. Fats and oils are also consumed as a result of absorption or incorporation in foods during baking and frying. The sharp increase in consumption of fast foods is a major contributor to the increase in the amount of dietary fat since fast foods rely extensively on frying processes employing fats and oils. In addition, the snack food industry uses large amounts of fats and oils in the production of potato chips, corn chips and other snack items.

It is clear that there is an enormous potential market for a fat substitute or fat mimetic that is substantially non-digestible or has reduced caloric value. Replacement of fats in the diet with non-caloric substitutes is a more efficient way of reducing caloric intake than replacing sugar or carbohydrates because, gram for gram, the substitution of non-caloric fat substitutes is more than twice as effective as reducing carbohydrate content with substances such as saccharine or aspartame.

One of the difficulties is eliminating fat from the diet is the fact that fats and oils are all-pervasive in food products. In part, this is because they play an important role in the organoleptic acceptability of food products. Generally speaking, a fat substitute providing fewer calories than a conventional triglyceride muse be non-digestible, that is, not hydrolyzed in the digestive tract. In addition, it should not be directly absorbed through the intestinal wall. While some types of fat substitutes may be non-digestible, they are not of sufficiently high molecular weight to prevent them from being absorbed through the intestinal wall. The threshold molecular weight of non-absorbability for lipophilic molecules appears to be about 600.

In addition, the fat substitute must itself be non-toxic at high levels of ingestion. It must contain no toxic residues or impurities. To the extent that a fat substitute may be partially hydrolyzed in the digestive tract, any hydrolysis products must be non-toxic and/or metabolizable. If metabolizable, they should have very low caloric value and toxicity. In general, fat substitutes must be without any serious physiological side effects.

A fat substitute must also have good organoleptic qualities of mouth feel and must not unacceptable alter the taste of food composition. In addition, fat substitutes must have appropriate physical properties for use in food compositions. For example, they should be liquids or low-melting solids depending on whether they are to be used as oil or shortening substitutes.

Another important requirement for a fat mimetic is sufficient resistance to oxidative and thermal degradation at elevated temperatures to permit the use of the fat mimetic in deep fat frying applications and other cooking applications. Among the problems which can result if a lipid is exposed to high temperatures for an extended period of time are discoloration, smoking, generation of volatile decomposition products, development of off-flavors and unacceptable odor, thickening or gelling due to cross-linking or polymer formation, production of toxic by-products, and so forth. Certain fat substitutes such as those derived from proteinaceous materials are not suitable for use in cooking since their fat-like properties are destroyed upon exposure to heat. Other fat substitutes, such as the esterified epoxide-extended polyols described in U.S. Pat. No. 4,861,613, are considerably more stable and thus are generally suitable for use in the preparation of cooked food. However, such compounds are still somewhat susceptible to degradation under severe conditions owing to the presence of readily-abstractable tertiary hydrogens in the poly(oxypropylene)segments of these materials. Thus, it would be highly desirable to obtain fat mimetics which are even more resistant to heat than esterified epoxide-extended polyols without sacrificing the desirable characteristics of low digestibility and fat-like properties exhibited by such substances.

SUMMARY OF THE INVENTION

This invention provides a fat mimetic comprising a mixture of esterified polyethers of the following structural formula,

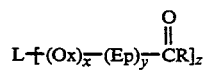

wherein L is an organic linking moiety, Ox is a ring-opened oxolane unit, ED is a ring-opened epoxide unit having an ester linkage to

which is substantially resistant to hydrolysis upon ingestion, x is from 0 to about 25 on average in the mixture with the proviso that when x is 0 the organic linking moiety is —O—(CH$_2$)$_4$—O—, y is from about 0.5 to 25 on average in the mixture, z is at least 2 on average in the mixture, and R is a C$_7$-C$_{23}$ hydrocarbon moiety.

The invention also provides a food composition having an edible oil component with reduced caloric availability wherein the edible oil component comprises an amount of a mixture of esterified polyethers of the structural formula given above effective to reduce the caloric content of the food composition as compared to a food composition containing a conventional triglyceride lipid.

The esterified polyethers of this invention are substantially non-digestible, non-absorbable, and non-toxic upon ingestion and yet exhibit physical and functional properties which are similar to conventional edible lipids. The instant fat mimetics have enhanced thermal stability and thus are exceptionally suitable for prolonged use at elevated temperatures in applications such as frying and cooking.

DETAILED DESCRIPTION OF THE INVENTION

The esterified polyethers of this invention are organic compounds comprised of four types of covalently bonded moieties, namely, (1) a linking moiety L, (2) a ring-opened oxolane unit Ox, (3) a ring-opened epoxide unit Ep, and (4) an acyl group

In order to minimize the amount of absorption through the intestinal wall, which can result in a higher than desired caloric availability, the number average molecular weight of the esterified polyether mixture should be at least about 600.

The presence of both the ring-opened oxolane units and the ring-opened epoxide units is critical to the desirable performance characteristics of the fat mimetics of this invention. Without wishing to be bound by theory, the ring-opened oxolane units apparently help to increase the thermal and oxidative stability of the fat mimetic since significantly lower stability is observed if the oxolane units are replaced by an equivalent number of ring-opened epoxide units. The presence of at least about one ring-opened epoxide unit between the ring-opened oxolane unit and the acyl group is similarly essential in that the fat mimetic is thereby rendered substantially resistant to hydrolysis and subsequent digestion upon internal consumption. In contrast, esterified poly(tetramethylene glycol) would not be suitable for use as a reduced calorie fat substitute since the ester groups present would be readily hydrolyzed owing to the primary structure of the terminal hydroxyl groups of poly(tetramethylene glycol). Thus, it has been discovered that in order to obtain a fat mimetic which is both heat resistant and substantially non-digestible, both types of moieties (oxolane and epoxide units) must be present.

The ring-opened oxolane unit has the skeletal formula

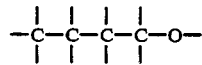

wherein the carbons are substituted with hydrogen or other substituents such as alkyl. The ring-opened oxolane unit is preferably derived from an oxolane, i.e., a cyclic ether containing four carbons and an oxygen atom in the ring. Preferred oxolanes include, for example, tetrahydrofuran, 2-methyltetrahydrofuran, 3-methyltetrahydrofuran, and the like and mixture thereof. Tetrahydrofuran is the most preferred oxolane due to its low cost, ease of polymerization, and stability of the ring-opened oxolane unit derived therefrom. The average number of ring-opened oxolane units in the esterified polyether mixture can be varied as desired to alter the physical, chemical, and organoleptic properties of the fat mimetic, but on average x in the structural formula given above will be from 0 to about 25. If x is 0, the linking moiety L must be a dioxytetramethylene moiety (i.e., —O—(CH$_2$)$_4$—O—). The preferred average range of x is from about 3 to 15. Higher ratios of oxolane units to epoxide units will generally tend to yield more thermally stable fat mimetics having higher melting or solidification points.

The ring-opened epoxide unit, on the other hand, has the skeletal formula —C—C—O— wherein the carbons are substituted with hydrogen or other substituents such as alkyl, aryl, aralkyl, and the like. The structure of the ring-opened epoxide unit adjacent to the acyl group is chosen such that the resulting ester linkage is substantially resistant to hydrolysis upon ingestion. The esterified polyether is thereby rendered non-digestible and suitable for use as a reduced calorie replacement for conventional triglyceride oils and fats which are hydrolyzed and digested upon ingestion. "Substantially resistant to hydrolysis" in this context means that a substance has an in vitro lipase hydrolysis rate value using porcine pancreatic lipase which is less than about 30% of the value of an olive oil standard. Preferably, the hydrolysis rate value is less than about 10% of the olive oil value. The experimental procedure for determining the in vitro lipase hydrolysis rate is described in U.S. Pat. No. 4,861,613, the teachings of which are incorporated herein by reference.

To render the esterified polyethers substantially resistant to hydrolysis in the digestive tract, the carbon connected to the ester group

should be at least about 50% (more preferably, at least about 85%) secondary and/or tertiary on average in the esterified polyether mixture. In other words, this carbon should be no greater than about 50 percent primary and most preferably is no more than about 15 percent primary on average. This key structural feature can be achieved by the use of a ring-opened epoxide unit adjacent to the acyl group having predominantly secondary and/or tertiary hydroxyl groups prior to formation of the ester linkage.

For these reasons, the ring-opened epoxide units are preferably derived from C$_3$-C$_9$ epoxides, i.e., cyclic ethers containing two carbon atoms and an oxygen atom in the ring and at least one carbon-containing substituent attached to one or more of the two ring carbons. Mixtures of epoxides may be employed if desired. Propylene oxide is the most preferred epoxide, but other epoxides such as 1,2-butene oxide, 2,3-butene oxide, isobutylene oxide, 1,2-pentene oxide, 1,2-hexene oxide, 1,2-heptene oxide, 1,2-octene oxide, phenyl glycidyl ether, cyclohexene oxide, cyclopentene oxide, methyl glycidyl ether, styrene oxide, allyl glycidyl ether, and ethyl glycidyl ether are also suitable. Minor amounts of ethylene oxide (an unsubstituted epoxide) may also be employed, but the use of this epoxide is generally not favored since it tends to yield primary ester linkages to the acyl group and also detracts from the fat-like properties of the esterified polyether owing to its hydrophilic character.

Sufficient ring-opened epoxide units are present in the esterified polyether mixture to render the fat mimetic substantially resistant to digestion. On average, therefore, the value of y in the structural formula given above should be at least about 0.5 and preferably is not higher than about 25. Preferably, y is from about 1 to 10.

The acyl group

in the esterified polyether has an R group which is a $C_7$-$C_{23}$ hydrocarbon moiety (more preferably, a $C_{11}$-$C_{21}$ hydrocarbon moiety). Preferably, this moiety is paraffinic or olefinic in structure. More preferably, the acyl group is derived from a fatty acid. Any of the known natural or synthetic fatty acids may be used, including, for example, caprylic, capric, lauric, myristic, myristoleic, stearic, palmitic, palmitoleic, rincinoleic, linoleic, linolenic, elaeostearic, arachidic, behenic, erucic, oleic, and heptadecanoic acid. The physical properties of the esterified polyether mixture may be varied as desired by changing the length and structure of hydrocarbon group R; products which are liquid oils, fats, greases, or solid waxes may thus be obtained. The fatty acid chain length is also believed to contribute to the low digestibility of the esterified polyether by making the composition substantially non-absorbable in the digestive tract. The fatty acids can be either synthetic or naturally occurring fatty acids and may be either saturated or unsaturated. For example, rapeseed oil provides a good source for $C_{22}$ acid (R=$C_{21}$). $C_{16}$-$C_{18}$ fatty acids (R=$C_{15-17}$) can be obtained from tallow, soybean oil, or cottonseed oil. Shorter chain fatty acids can be provided by coconut, palm kernel oil, or babassu oils. Corn oil, fish oil, lard, olive oil, palm oil, peanut oil, safflower seed oil, sesame seed oil, jojoba oil and sunflower seed oil are examples of other natural oils which can serve as the source of the fatty acid component. Among the fatty acids, those that are preferred have from about 14 to about 22 carbon atoms (R=$C_{13-21}$), and are most preferably selected from the group consisting of myristic, palmitic, stearic, oleic, behenic, and linoleic. The preferred sources for the fatty acid components are natural fats and oils which have a high content of these fatty acids, e.g., soybean oil, rapeseed oil, olive oil, cottonseed oil, corn oil, tallow and lard.

The structure of the linking moiety L is not critical and can be any moiety which covalently links the

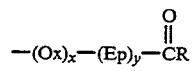

branches of the esterified polyether. Preferably, the linking moiety does not contain any readily hydrolyzed ester groups or other hydrolyzable functionalities which could increase the digestibility of the esterified polyether to an unacceptable level. For reasons of convenience in the preparation of the fat mimetics of this invention, as will be explained subsequently, L is most preferably —O—$(CH_2)_4$—O—.

The esterified polyethers of this invention may be prepared by any appropriate synthetic method. One such method involves first polymerizing one or more oxolanes to form an oxolane polyether polyol, alkoxylating the oxolane polyether polyol with the desired number of equivalents of the epoxide to form an epoxide/oxolane polyether polyol, and then esterifying the epoxide/oxolane polyether polyol by reacting with one or more fatty acids or fatty acid derivatives. Alternatively, a 1,4-alkanediol such as 1,4-butanediol or an oligomeric condensate thereof may be used as a starting material.

The preparation of oxolane polyether polyols is well-known in the art and typically is carried out using a cationic initiator. Such methods are described, for example, in Inoue, et al., "Cyclic Ethers" in *Ring-Opening Polymerization*, Vol. 1, Ivin et al., Ed., Elsevier, pp. 185-298(1984).

The teachings of these references are incorporated herein by reference in their entirety. Minor amounts of epoxides such as ethylene oxide or propylene oxide can be incorporated in a random fashion in the oxolane polyether polyol if desired. Although generally the use of oxolane polyether polyols wherein the linking moiety L is —O—$(CH_2)_4$—O— and z is 2 is preferred due to the ease with which such compounds may be obtained, other oxolane polyether polyols wherein z is greater than 2 may also be employed. The synthesis of "star" or branched oxolane polyether polyols using a variety of linking moieties is well-known and is described, for example, in the following references; Cai, et al., *Makromol. Chem.* 187. 553(1986), Franta et al., *J. Polym. Sci., Polym. Symp.* 56, 139(1976) Tezuka, et al., *Polym. Prepr., Am. Chem. Soc. Div. Polym. Chem.* 22, 313(1981), and Hammond et al., *Weapons Res. Estab., Rep.*, WRE-TN-CPD-146(1968).

Oxolane polyether polyols are also available commercially from sources such as BASF Corp. ("POLYTHF"), E.I. du Pont de Nemours ("TERETHANE"), and QO Chemicals ("POLYMEG"). Molecular weights of the commercially available oxolane polyether polyols range from 650 to 2900 on average.

The alkoxylation step is preferably performed by reacting the oxolane polyether polyol, 1,4-alkanediol, or 1,4-alkanediol oligomer with the epoxide or mixture of epoxides in the presence of a catalyst. Any of the large number of alkoxylation catalysts known in the art may be used for this purpose, preferably a catalyst which will tend to promote ring-opening of the epoxide so as to provide secondary or tertiary hydroxyl end-groups. Basic catalysts and coordinate anionic catalysts are preferred for this reason since attack of the primary hydroxyl end-groups of the oxolane polyether polyol intermediate will predominantly occur at the less substituted carbon of the epoxide ring.

A basic catalyst may preferably be selected from the group consisting of basic alkali metal compounds, basic alkaline earth compounds, and basic tertiary amines. Suitable alkali metal and alkaline earth catalysts include the hydrides, carbonates, oxides, hydroxides, carboxylates, alkoxides, and sulfates of lithium, sodium, potassium, barium, calcium, and strontium as well as the elemental forms of the metals (e.g., sodium or potassium metal dispersions). Generally speaking, it is desirable to pre-react the oxolane polyether polyol with the alkali metal or alkaline earth catalyst to form the salt of the oxolane polyether polyol prior to reaction with the epoxide. For example, if sodium hydroxide or potassium hydroxide is employed as the catalyst, a mixture of the oxolane polyether polyol and catalyst may be heated under conditions such that the water formed by reaction of the components is removed and the alkali metal salt of the oxolane polyether polyol is formed.

Suitable tertiary amines for use in this process include aliphatic, aromatic, and mixed aliphatic-aromatic amines such as triethylamine, N,N-dialkyl anilines, dimethylaminocyclohexane, tri-n-propylamine, tetraethyl ethylenediamine, N,N'-dialkylpiperazines, N-alkylpiperidines, pyridine and substituted pyridines, N-alkyl pyrrolidinones, quinuclidine, and the like.

The amount of basic catalyst employed must be sufficient to effectively catalyze the addition of the epoxide to the hydroxyl group(s) of the oxolane polyether polyol, 1,4-alkanediol, or 1,4-alkanediol oligomer. Preferably this amount is from about 0.01 to 1 equivalent of basic catalyst per equivalent of hydroxyl groups in the oxolane polyether polyol or other starting material. The epoxide and oxolane polyether polyol are preferably reacted at a temperature of from about 50° C. to 175° C. for a time effective to accomplish substantial (e.g., over 25%) conversion of the epoxide. Reaction times of from 1 to 48 hours will typically suffice. The molar ratio of epoxide to oxolane polyether polyol or other starting material may be varied as desired depending upon the number of ring-opened epoxide units desired in the final esterified polyol, but generally from about 0.5 to 25 equivalents of epoxide per equivalent of hydroxyl groups in the oxolane polyether polyol or other starting material will be typically employed. It is generally desirable to add the epoxide incrementally with agitation to the oxolane polyether polyol (or other starting material) and basic catalyst. The alkoxylation may be carried out in the presence of an inert organic solvent. When the desired degree of epoxide conversion has been achieved, the epoxide/oxolane polyether polyol may be purified by removing any unreacted epoxide using a suitable method such as vacuum stripping. The epoxide/oxolane polyether polyol may also be treated to remove the residual basic catalyst. Methods such as filtration, distillation, extraction, precipitation, or absorption can be used depending on the particular catalyst employed. Any of the standard methods for removing a basic catalyst from an alkoxylated product may be employed. If an alkali metal or alkaline earth catalyst is present, for example, a particularly advantageous method of catalyst removal involves heating the product with magnesium silicate to absorb the metal and then filtering to remove the magnesium silicate. However, it may also be desirable to leave the basic catalyst in the epoxide/oxolane polyether polyol so that it may serve as a catalyst in the subsequent esterification step.

Alternatively, a coordinate anionic catalyst may be utilized to achieve alkoxylation of the oxolane polyether polyol, 1,4-alkanediol, or 1,4-alkanediol oligomer. Examples of suitable anionic catalysts include the class of catalysts known as double metal cyanide complex catalysts (e.g., zinc hexacyanocobaltate/zinc chloride/glyme/water). The preparation of alkoxylated oxolane polyether polyols using catalysts of this type is described fully in U.S. Pat. No. 3,829,505, which is incorporated herein by reference in its entirety.

The esterification of the intermediate epoxide/oxolane polyether polyol may be accomplished using any suitable method known for synthetic transformations of this type. For example, a fatty acid or mixture of fatty acids may be reacted with the epoxide/oxolane polyether polyol to yield the esterified polyether product and water as a co-product. A catalyst may be used to accelerate the reaction, preferably an acidic catalyst such as a mineral acid (sulfuric acid, for example) or a sulphonic acid (p-toluene sulphonic acid, for example). The water co-product may be removed continuously from the reaction mixture using a method such as azeotropic distillation in order to drive the reaction to completion. Alternatively, a transesterification reaction may be employed wherein a fatty acid ester

or mixture of fatty acid esters is reacted with the epoxide/oxolane polyether polyol. Preferably, the fatty acid ester contains a $C_1-C_6$ alkoxy moiety ($R'=CH_3$, for example). The low boiling alcohol formed as a coproduct may be removed from the transesterification reaction mixture in order to drive the equilibriums reaction to completion in the desired direction. A catalyst such as an acidic or basic catalyst may be used in the transesterification. In yet another approach, the epoxide/oxolane polyether polyol may be reacted with an acid halide derivative of one or more fatty acids

wherein X=Cl, Br, etc.,].

The epoxide/oxolane polyether polyol and the fatty acid compound are reacted for a time and at a temperature sufficient to accomplish esterification of the hydroxyl groups of the epoxide/oxolane polyether polyol. It is not necessary to achieve complete esterification in the esterified polyethers of this invention. In fact, it may be desirable to leave some portion of the hydroxyl groups unesterified to vary certain properties of the fat mimetics such as their tendency to promote anal leakage or short bowel transit times. Preferably, however, at least about 90% of the hydroxyl groups in the intermediate epoxide/oxolane polyether polyol are esterified. The optimum reaction conditions will vary somewhat depending upon the particular type of fatty acid compound used. If a fatty acid or fatty acid ester is utilized, the reaction temperature is preferably from about 100° C. to 350° C.; reaction times of from about 1 to 48 hours are generally sufficient to effect esterification of the hydroxyl groups. When the fatty acid moiety is a fatty acid halide, somewhat lower reaction temperatures (e.g., about 25° C. to 125° C.) are sufficient, particularly if a tertiary amine such as triethylamine is additionally present to take up the HX generated during the esterification reaction. Reaction times of from about 1 to 48 hours are typically sufficient.

To accomplish substantially complete esterification of the epoxide/oxolane polyether polyol, at least about 1 (more preferably, at least about 1.1) equivalent of the fatty acid compound per equivalent of hydroxyl groups in the epoxide/oxolane polyether polyol are used. For reasons of economy, it is preferred to react not more than about 3 equivalents of fatty acid compound. Any excess fatty acid compound may be removed from the esterified polyether product by an appropriate method such as vacuum steam stripping.

It should be understood that by the nature of the chemical reactions used to prepare the esterified polyethers of this invention, the products obtained will typically be mixtures of individual compounds which have a range of molecular weights and which may contain structural isomers. It may be useful to deliberately blend individually prepared esterified polyethers having different proportions of oxolane units and epoxide units, different functionality (varying values of z) and/or different R substituents in order to obtain fat mimetics having certain desired properties.

The esterified polyethers of this invention may be used as partial or total replacements for conventional lipids in any edible fat-containing food composition. The amount of the fat mimetic employed is sufficient to effectively reduce the available calories of the food composition compared to a food composition prepared using a conventional fully digestible triglyceride lipid. Preferably, at least about 10 percent (more preferably, at least about 25 percent) of the edible oil component of the composition is comprised of the esterified polyether. The fat substitute of this invention can replace a triglyceride lipid in a cooking oil, frying oil, salad oil or shortening, for example. Additional uses include combining the esterified polyethers with other ingredients to form food compositions such as cakes, breads, ice cream, candy, sour cream substitutes, mayonnaise, margarine, cheese and cheese spreads, cold cuts, potato chips, and the like. Illustrative ingredients which may be used in combination with the fat mimetics of this invention include carbohydrates (starches, sugars, celluloses), edible lipids (triglycerides), proteins (from animal or vegetable sources), vitamins antioxidants, emulsifiers, thickeners, preservatives, colorants, flavors, fragrances, sugar substitutes, water, milk, spices, eggs, and the like. The instant esterified polyethers of this invention are particularly suitable for the preparation of food compositions requiring exposure to elevated temperatures. Unlike other proposed fat substitutes such as proteinaceous macrocolloids or unesterified polyoxypropylene polyols, the fat mimetics of this invention are exceptionally stable thermally and do not readily decompose or lose their fat-like properties when heated. They are therefore ideally suited for application such as deep fat frying.

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the fat mimetics and food compositions of this invention, but are not limitative of the invention in any manner whatsoever.

EXAMPLES 1–6

These examples demonstrate the preparation of epoxide/oxolane polyether polyols useable as precursors for the esterified polyether fat mimetics of this invention.

In Example 1, a polytetrahydrofuran diol obtained from a commercial source (1000 parts by weight; average molecular weight = 1000; average degree of polymerization = ca. 14) was heated under vacuum at 100°–110° C. with ca. 5 parts by weight potassium hydroxide until water evolution ceased. Propylene oxide (464 parts) was added continuously at 95°–100° C. while maintaining an autogenous pressure in the reaction vessel of 40–70 psi. After the addition was completed, the reaction mixture was purged with nitrogen and heated with magnesium silicate to remove the alkali metal catalyst. The product after filtration was a colorless liquid corresponding to the structural formula shown in Table 1.

By following the procedure described above for Example 1, epoxide/oxolane polyether polyols containing varying amounts of ring-opened propylene oxide units were prepared using polytetrahydrofuran diols of different molecular weights. The compositions of these products are given in Table 1.

TABLE 1

$$H\mathord-\!(\!O\mathord-\!CH\!-\!CH_2)_y\!-\!(O(CH_2)_4)_x\!-\!O\!-\!(CH_2)_4\!-\!O\!-\!(CH_2)_4\!-\!O)_{x^1}\!-\!(CH_2CHO)_{y^1}H$$
(with CH₃ substituents on the CH groups)

| Example | Hydroxyl No., (mg KOH/g) | $x, x^1$ (ave) | $y, y^1$ (ave) |
|---|---|---|---|
| 1 |  | 6.5 | 4 |
| 2 | 102 | 6.5 | 0.9 |
| 3 | 85.6 | 6.5 | 0.9 |
| 4 | 143 | 4 | 1 |
| 5 | 108 | 4 | 3.4 |
| 6 | 82.9 | 4 | 6 |

EXAMPLE 7

This example demonstrates the preparation of an esterified polyether fat mimetic in accordance with the invention.

The epoxide/oxolane polyether polyol product from Example 1 (1464 parts by weight) was mixed with oleic acid (733 parts) and heated to 240° C. under a nitrogen purge. After attaining a hydroxyl conversion of greater than 95%, the product was diluted with hexane, treated with aqueous potassium hydroxide to neutralize the excess fatty acid, and filtered to remove the precipitated fatty acid salt. After removal of the solvent by vacuum distillation, the fatty acid salt level was reduced further by heating with magnesium silicate at 90° C. for 2 hours. The esterified polyether product obtained after filtration was a clear, light yellow oil with the characteristic appearance, odor, and taste of a typical refined vegetable oil. The average chemical composition of the fat mimetic was found to be

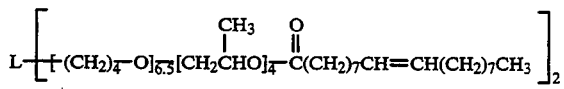

wherein L is —O—(CH$_2$)$_4$—O—.

EXAMPLE 8

The procedure of Example 7 was repeated using the epoxide/oxolane polyether polyol of Example 2 (1100 parts) and oleic acid (640 parts). The esterified polyether fat mimetic produced was clear, light yellow liquid having the characteristic appearance, odor, and taste of vegetable oil and the following average chemical composition:

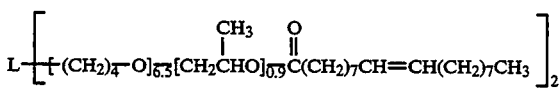

wherein L is —O—(CH$_2$)$_4$O—.

EXAMPLE 9

The procedure of Example 7 was repeated using the epoxide/oxolane polyether polyol of Example 6 (785 parts) and oleic acid (650 parts). The esterified polyether product was similar in taste, odor, and appearance to the products of Examples 7 and 8 and had the average chemical composition.

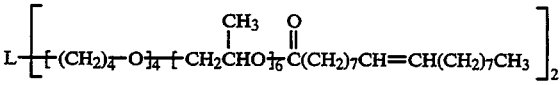

wherein L is —O—(CH$_2$)$_4$—O—

EXAMPLE 10

To demonstrate the enhanced thermal and oxidative stability of the fat mimetics of this invention, the esterified polyether product of Example 7 (200 g) was placed in 10" metal container producing a film of approximately 0.39 g/cm$^2$. The temperature was increased to 190° C. and the weight of the fat mimetic measured after 1 and 4 hours. After the first hour, a slight weight loss of only 0.7% was observed. After a total heating time of 4 hours, the amount of weight loss was still just 2.2%. The esterified polyether product remained light in color and produced a minimal amount of smoke. The odor of the heated esterified polyether resembled that of a conventional digestible triglyceride oil. Upon cooling to room temperature, the fat mimetic was found to have retained its oil-like properties and consistency.

COMPARATIVE EXAMPLE 11

To demonstrate the improved stability of the fat mimetics of the instant invention, the procedure of Example 10 was repeated using an esterified propoxylated glycerin composition prepared in accordance with the teachings of U.S. Pat. No. 4,861,613 using 550 molecular weight propoxylated glycerin and oleic acid. After 2 hours at 190° C. the weight loss observed was 2.2%. A weight loss of 3.7% had occurred after 4 hours.

This difference in stability was particularly surprising since the esterified propoxylated glycerin composition of this example had a much lower weight proportion of polyether than the esterified polyether product of Example 10 (ca. 35% vs. 60%). Given the known susceptibility of aliphatic polyethers in general towards thermal and oxidative degradation, the fat mimetic containing more polyether would have been expected to be less stable at elevated temperatures.

EXAMPLE 12

The alkoxylation procedure of Example 1 is repeated using 250 parts by weight polytetrahydrofuran having an average molecular weight of 250 (functionality=2; average degree of polymerizations=ca. 3.5) and 1,2-butene oxide (144 parts by weight). The epoxide/oxolane polyether polyol thus obtained (394 parts) is then reacted with an excess of stearic acid (711 parts) using the conditions described in Example 7. The product obtained is expected to be a reduced calorie fat mimetic having the average chemical composition:

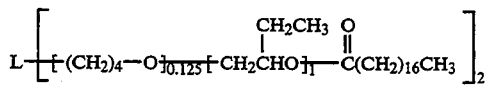

wherein L is —O—(CH$_2$)$_4$—O—.

EXAMPLE 13

Polytetrahydrofuran (2000 parts by weight) having an average molecular weight of 2000 ("POLYMEG") polytetramethylene ether glycol available from QO Chemicals; functionality=2; average degree of polymerization=ca. 27.8) is reacted with a mixture of ethylene oxide (88 parts) and propylene oxide (646 parts) using the procedure of Example 1. Esterification of the resulting epoxide/oxolane polyether polyol is then performed using a 20% molar excess of coconut fatty acid (Emery 621 grade, available from the Emery Group of Henkel Corp.) and the conditions of Example 7. The product obtained after purification is expected to be a thermally stable fat mimetic having reduced caloric availability and the average chemical composition:

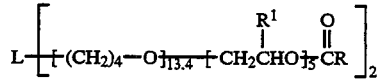

wherein L is —O—(CH$_2$)$_4$—O—, the acyl group

is derived from the coconut fatty acid (a mixture of primarily lauric, capric, myristic, palmistic, and oleic acids), and R$^1$ is either hydrogen or methyl (the ratio of hydrogen to methyl being 1:4).

EXAMPLE 14

Polytetrahydrofuran containing about 15 weight percent ethylene oxide is prepared in accordance with the teachings of U.S. Pat. No. 4,728,722 (Example 1). The average molecular weight of the polytetrahydrofuran is about 1260. The polytetrahydrofuran (1260 parts by weight) is reacted with propylene oxide (232 parts) using the procedure of Example 1. Esterification of the resulting epoxide/oxolane polyether polyol (1492 parts)

is then carried out using a 25% molar excess of soya fatty acid ("INDUSTRENE" 226, available from the Humko Chemical Division of Witco Corp.) and the conditions of Example 7. The product obtained after purification is expected to be a reduced calorie fat substitute having superior thermal stability and the average chemical composition:

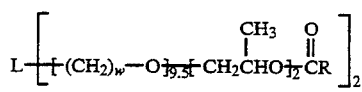

wherein L is —O—(CH$_2$)$_4$—O—, the acyl group

is derived from the soya fatty acid, and w is either 2 or 4, with the molar ratio of ethylene oxide:tetrahydrofuran ring-opened units being ca. 0.3 on average.

EXAMPLE 15

This example demonstrates the preparation of reduced calorie french fries using the esterified polyether of this invention.

Potatoes are pared and then cut lengthwise in strips approximately ⅜ inch in width. The esterified polyether product of Example 7 is heated to 360° F. in a suitable deep-fat cooking vessel; sufficient fat mimetic is employed to provide a layer at least about 2 inches deep in the vessel. The cut potato strips are placed in the hot fat mimetic for 6 to 7 minutes or until crisp and golden, then drained on paper towels and sprinkled with salt.

The french fries thus prepared are expected to be similar in taste, odor, and appearance to french fries prepared using a conventional triglyceride oil. However, their available caloric content is significantly reduced owing to the substantially non-digestible and non-absorbable character of the esterified polyether fat mimetic.

EXAMPLE 16

The preparation of a carrot-pineapple cake using the esterified polyether fat mimetic of this invention is illustrated by this example.

Sifted all-purpose flour (1½ cups), sugar (1 cup), baking powder (1 tsp.), baking soda (1 tsp.), ground cinnamon (1 tsp.), and salt (¼ tsp.) are sifted together in a bowl. The esterified polyether product of Example 8 (⅔ cup), eggs (2), finely shredded carrot (1 cup), crushed pineapple with syrup (¼ cup), and vanilla (1 tsp.) are then added and mixed until moistened. The mixture is beaten 2 minutes at medium speed using an electric mixer, placed in a greased and floured 9×9×2 inch pan, and baked at 350° F. for 35 minutes or until done. The cake is cooled 10 minutes and removed from pan. The cake thus prepared is expected to be similar in taste, odor, appearance, and texture to a cake prepared using soybean oil instead of the esterified polyether, yet is substantially lower in available calorie content due to the hydrolysis- and absorption-resistance of the fat mimetic.

I claim:

1. An esterified polyether of the following structural formula, useful as a reduced calorie fat replacement in a food composition:

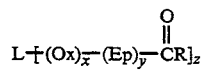

wherein L is an organic linking moiety, Ox is a ring-opened oxolane unit, Ep is a ring-opened epoxide unit having an ester linkage to

which provides said esterified polyether with an in vitro lipase hydrolysis rate value using porcine pancreatic lipase which is less than about 30% of the value of an olive oil standard., x is from 3 to 25, y is from 1 to 25, z is at least 2, and R is a C$_7$–C$_{23}$ hydrocarbon moiety.

2. The esterified polyether of claim 1 wherein the ring-opened oxolane unit Ox is derived from an oxolane selected from the group consisting of tetrahydrofuran, 2-methyltetrahydrofuran, 3-methyltetrahydrofuran, and mixtures thereof.

3. The esterified polyether of claim 1 wherein the ring-opened epoxide unit Ep is derived from a C$_3$–C$_9$ epoxide.

4. The esterified polyether of claim 1 wherein the

acyl group is derived from a fatty acid.

5. The esterified polyether of claim 1 wherein Z is 2.

6. The esterified polyether of claim 1 wherein the linking moiety L is —O—(CH$_2$)$_4$—O—.

7. The esterified polyether of claim 1 wherein the ring-opened oxolane unit is derived from tetrahydrofuran.

8. The esterified polyether of claim 1 wherein the ring-opened epoxide unit is derived from propylene oxide.

9. An esterified polyether of the following structural formula, useful as a reduced calorie fat replacement in a food composition:

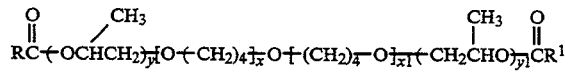

wherein x and x$^1$ are each independently from 3 to 25, y and y$^1$ are each independently from 1 to 10, and R and R$^1$ are each independently a C$_{11}$–C$_{23}$ paraffinic or olefinic hydrocarbon moiety.

10. The esterified polyether of claim 9 wherein

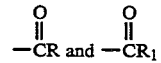

are each derived from a fatty acid.

11. A food composition having an edible oil component with reduced caloric availability wherein the edible oil component comprises an amount of an esterified polyether effective to reduce the caloric content of the food composition, the esterified polyether having the structural formula:

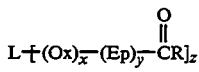

wherein L is an organic linking moiety, Ox is a ring-opened oxolane unit, Ep is a ring-opened epoxide unit having an ester linkage to

which provides said esterified polyether with an in vitro lipase hydrolysis rate value using porcine pancreatic lipase which is less than about 30% of the value of an olive oil standard, x is from 3 to 25, y is from 1 to 25, z is at least 2, and R is a $C_7$–$C_{23}$ hydrocarbon moiety.

12. The food composition of claim 11 wherein the ring-opened oxolane unit Ox is derived from an oxolane selected from the group consisting of tetrahydrofuran, 2-methyl tetrahydrofuran, 3-methyl tetrahydrofuran, and mixtures thereof.

13. The food composition of claim 11 wherein the ring-opened oxolane unit Ox is derived from tetrahydrofuran.

14. The food composition of claim 11 wherein the ring-opened epoxide unit Ep is derived from a $C_3$–$C_9$ epoxide.

15. The food composition of claim 11 wherein the ring-opened epoxide unit Ep is derived from propylene oxide.

16. The food composition of claim 11 wherein

acyl group is derived from a fatty acid.

17. The food composition of claim 11 wherein z is 2.

18. The food composition of claim 11 wherein the linking moiety L is —O—$(CH_2)_4$—O—.

19. A food composition having an edible oil component with reduced caloric availability wherein from 10 to 100% of the edible oil component is comprised of an esterified polyether having the structural formula:

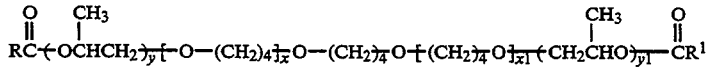

wherein x and $x^1$ are each independently from 3 to 25, y and $y^1$ are each independently from 1 to 10, and R and $R^1$ are each independently a $C_{11}$–$C_{23}$ paraffinic or olefinic hydrocarbon moiety.

20. The food composition of claim 19 wherein

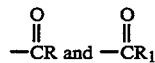

are each derived from a fatty acid.

* * * * *